United States Patent [19]

Barbarisi

[11] Patent Number: 4,943,986
[45] Date of Patent: Jul. 24, 1990

[54] MAMMOGRAPHY COMPRESSION APPARATUS FOR PROSTHETICALLY AUGMENTED BREAST

[76] Inventor: Leonard Barbarisi, 2034 E. Sourthern, Ste. D, Tempe, Ariz. 85282

[21] Appl. No.: 263,520
[22] Filed: Oct. 27, 1988
[51] Int. Cl.⁵ .............................................. A61B 6/04
[52] U.S. Cl. ...................................... 378/37; 378/208
[58] Field of Search ................................. 378/37, 208

[56] References Cited

U.S. PATENT DOCUMENTS 3,971,950  7/1976  Evans et al. .......................... 378/37
4,563,768  1/1986  Read et al. ........................... 378/37

FOREIGN PATENT DOCUMENTS 403400  of 1974  U.S.S.R. ................................ 378/37

Primary Examiner—Craig E. Church
Attorney, Agent, or Firm—Gregory J. Nelson

[57] ABSTRACT

An improved mammographic apparatus for patients having prosthetically augmented breasts. The apparatus has an X-ray source with an upper breast compression and lower compression plate mounted in one X-ray path. The anterior surface of the compression plates adjacent the patient are curved and sloped conforming to the patient's anatomy to avoid trapping the prosthetic envelope of patients during compression of the breast. In one embodiment, the wall surface of the compression plates adjacent the patient are pliable to allow medical personnel to conform the walls of the plates to the anatomy of the patient. The film holder associated with the lower compression plate may be modified so it may be loaded from below the lower compression plate or from the rear to accept a specially shaped film cassette.

12 Claims, 3 Drawing Sheets

MAMMOGRAPHY COMPRESSION APPARATUS FOR PROSTHETICALLY AUGMENTED BREAST

BACKGROUND OF THE INVENTION

The present invention relates generally to a mammography apparatus and more particularly to an improved upper and lower compression plate arrangement for applying compression to the augmented breast during mammographic examination.

Mammography is an X-ray examination technique used to detect and discover anomolies of the female breast, including lumps, distortions or calcification in the tissue. It is general practice to apply vigorous compression to the breast to improve the quality, contrast and sharpness of the resulting X-ray picture. Various devices can be found in the prior art for applying pressure to the breast during such examinations, however, none address the problem of mammography examination of prosthetically augmented breasts. For example, U.S. Pat. No. 3,824,397 shows a device in which pressure is applied to a plastic sheet which is placed on the breast.

U.S. Pat. No. 4,090,084 relates to a mammography apparatus having a pressure plate which is mounted so that the pressure can be applied uniformly throughout the breast area. To enable such uniform pressure to be obtained, the pressure plate is connected at its opposite ends to a slide which is mounted on tracks on the cone of the X-ray machine.

U.S. Pat. No. 4,259,585 describes a device in which a compression plate is mounted parallel to the support plate and is adjustable relative to the support plate to adjust the spacing therebetween. The compression plate is provided with a cut-out area. At the margin of the cut-out section, marking is provided which is reproducible on the X-ray film for locating a specific point in the cut-out section.

U.S. Pat. No. 4,122,350 suggests the use of a collimating device provided to restrict the X-rays. The collimator is designed to fit closely over the breast, the collimator being adjustable.

While various mammography compression devices are suggested in the prior art, they do not provide appropriate compression of the breast tissue in patients who have undergone breast augmentation procedures involving the placement of prosthetic implants behind the breast tissue.

A particular problem occurs with patients who have had breast augmentations with implants. It is estimated that over a million women nave undergone augmentation mammaplasty in the United States. The breast implant generally consists of a silicon gel or saline solution encapsulated within a flexible envelope. The implant is effectively radiographically opaque.

With conventional dedicated mammography systems the lower support table is generally fixed and the upper plate is movable to apply compression to the breast. As the movable compression plate is lowered to apply compression to the breast, the prosthesis also becomes entrapped along with the breast tissue, totally or partially obscuring portions of the breast tissue and thus degrading or interfering with the resulting X-ray photograph. For a discussion of the effects of breast prosthesis on the screening technique see "Mammograph and Breast Implants" in Plastic and Reconstructive Surgery, July, 1988, Vol. 82, No. 1, Pages 1-7.

Accordingly, in view of the foregoing, it is a primary object of the present invention to provide an improved mammography compression apparatus which facilitates the taking of satisfactory mammographs in patients who have undergone augmentation mammaplasty.

Another object of the present invention is to provide mating upper and lower compression plates for X-ray mammography, which plates are cooperatively contoured to avoid trapping the prosthetic envelope during the compression of the breast tissue. The compression plate may be provided as original equipment or may be appropriately adapted to an existing X-ray apparatus.

Another object of the present invention is to provide compression plates for a mammography X-ray system having relieved areas which allow the plates to pass along the prosthesis without trapping the prosthesis therebetween.

SUMMARY OF THE INVENTION

A conventional mammography apparatus has a fixed lower support table which holds a film cassette and an upper compression plate is movable relative to the support table and attached to the machine at an appropriate attachment arm. In accordance with the present invention, an X-ray mammography compression apparatus is provided having improved upper and lower compression plates of a suitable X-ray compatible material. The upper plate replaces the conventional compression plate and the lower plate is secured on the top surface of the lower support table by a suitable fastener or clamp. The inner or anterior walls of the compression plates (the walls adjacent the patient) are contoured to define a relieved area in the plates which allow the breast tissue to be selectively compressed without trapping the prosthesis and thus avoid obscuration of the X-ray by the prosthesis. The anterior walls of the plates are preferably sloped conforming to the patient's anatomy to provide intimate contact the patient's skin and thus assist in drawing the breast tissue away from the prosthesis.

In another embodiment of the invention, the compression plates are configured as a plurality of relatively movable strips. The anterior ends of the plates are connected to a pliable wall so the configuration of the relieved area defined by the wall can be varied in accordance with the anatomical requirements of the patient.

In still another embodiment the conventional support plate is replaced by a lower compression plate having a relieved anterior edge. The lower compression plate has a magazine for accepting a specially shaped film cassette for closer positioning of the breast tissue to the film. This arrangement replaces the combination of the standard lower table and the improved lower compression plate secured to the top of the table.

The above and other objects, features and advantages of the present invention will become more apparent from the following detailed description taken in conjunction with the drawings in which:

DETAILED DESCRIPTION OF THE PREFERRED EMBODIMENTS

Figure 1:
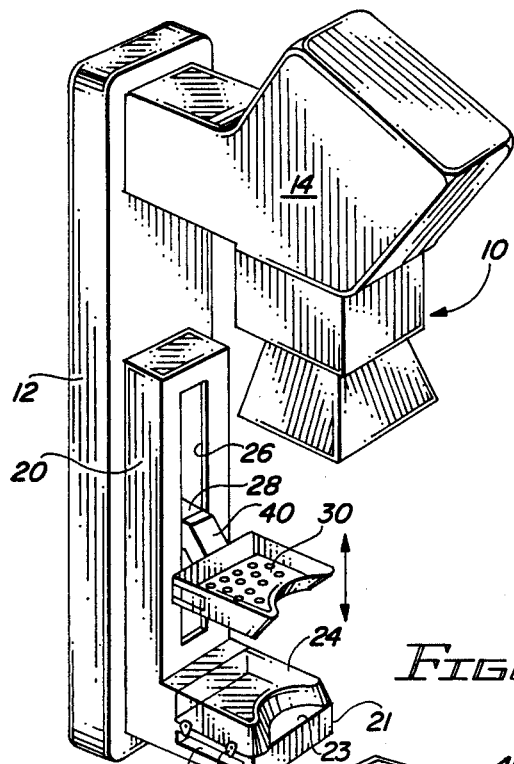
FIG. 1 is a perspective view illustrating a conventional dedicated X-ray examination machine having upper and lower compression plates attached thereto in accordance with the present invention.

Turning now to the drawings, FIG. 1 illustrates a conventional dedicated X-ray machine having the compression plates of the present invention attached thereto. The X-ray apparatus is generally designated by the numeral 10 and includes a vertical cabinet 12 including vertical column 20 having an X-ray source housing 14 arranged at its upper end. The housing 14 contains the X-ray source and associated controls which form no particular part of the present invention and detailed description is not necessary as they are conventional and well known in the art. The X-ray source emits a stream of X-rays downwardly as indicated to provide an X-ray photograph by exposing special low radiation exposure film. The Thomson-CGR Senographe 500 TX dedicated mammography system is representative of apparatus of this general type.

Support table 21 extends from the lower end of column 20 having an upper horizontal support surface 23. A recess or film magazine 22 is provided in the support table for receiving a film cassette which is exposed by the X-ray source to provide an X-ray photograph of the patient's breast. A lower compression plate 24 is supported on table 21 by appropriate retainer clips 27. Compression plate 24, as will be explained in detail hereafter, is specially designed to apply compression to patients having breast implants.

Oppositely disposed above the lower compression plate 24 is upper compression plate 30. Compression plate 30 is supported on arm 28 of the X-ray machine which arm is received within vertical slot 26 of column 20. Arm 28 is vertically adjustable by means of a manual or motor-driven mechanism such as a screw jack for adjusting the relative spacing between the compression plates 24 and 30.

The present invention deals specifically with the design of the lower compression plate 24 and the upper compression plate 30. As shown in FIG. 1, the lower compression plate 24 is fixed and the upper plate 30 is vertically adjustable. However, it is within the scope of the invention for the upper plate t be fixed and the lower plate adjustable or, in some cases, both plates may be adjustable to apply the necessary compression.

Figure 3:
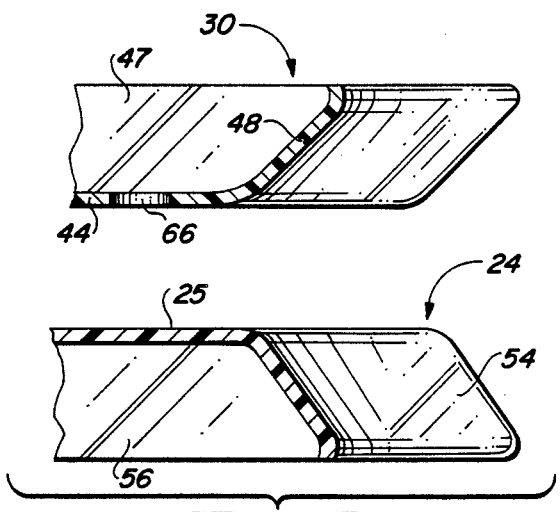
FIG. 3 is a partial sectional view of the upper and lower compression plates taken along section line 3—3 of FIG. 2.
Figure 2:
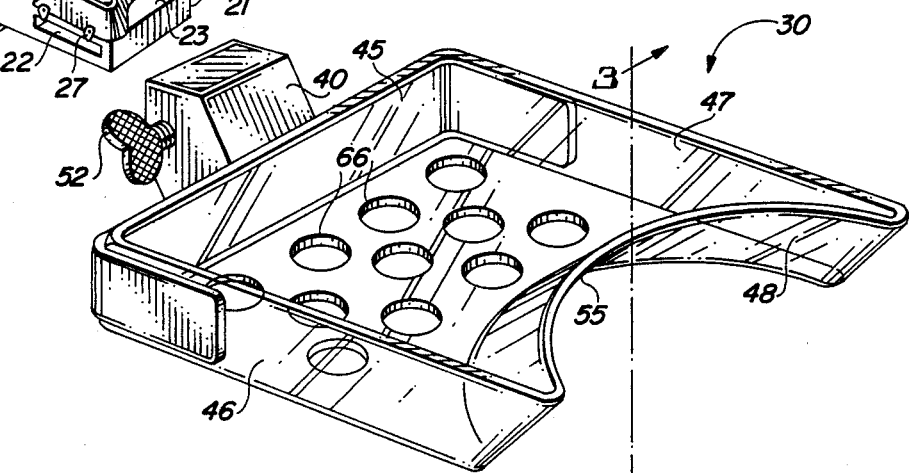
FIG. 2 is an enlarged perspective view illustrating the upper and lower compression plates.
Figure 2:
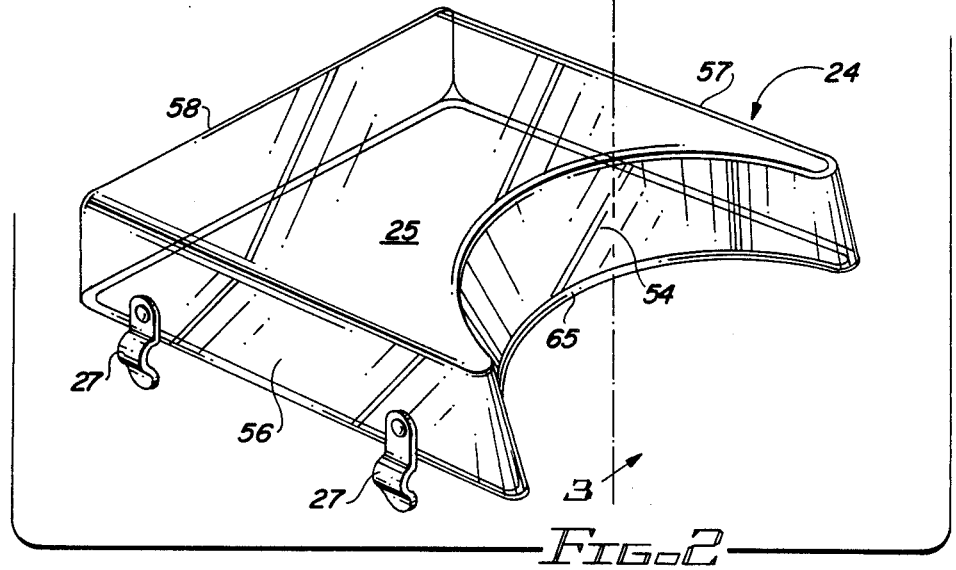

The details of the compression plates are best seen in FIGS. 2 and 3. As shown, upper compression plate 30 has a lower compression wall 44, posterior wall 45, opposite side walls 46 and 47 and anterior wall 48. As used herein, the term "rear" or "posterior" refers to an orientation away from the patient and "front" or "anterior" refers to an orientation adjacent the patient. For screen-film mammography, best results are obtained when compression surface 44 is generally parallel to the surface of the film in the film holder or magazine 22.

Compression plate 30 may be formed of any suitable material but is preferably transparent to assist the medical personnel in the examination and screening procedure and also to prevent any interference with passage X-rays. For this purpose, the plate 30 may be a material such as clear polymeric material, lucite, or plexiglas and may be fabricated by convenient means such as injection molding or vacuum forming. Compression plate 30 is secured to the X-ray machine by means of connector 40 which is formed as an integral extension of the plate. Connector 40 extends rearwardly from the center of the compression plate and is shown as being a generally tubular member defining a receiver section which may be attached to vertically adjustable arm 28 of the X-ray machine. Connector 40 and arm 28 can be detachably secured to the X-ray apparatus by any convenient mechanical fastener such as a set screw 52 so that the compression plate can be easily removed in the event the attending medical personnel wish to attach a plate of different type or configuration to the X-ray machine.

The anterior wall 48 of the compression plate 30 has a generally transversely curved configuration defining a relieved area 55 at the anterior edge of the plate. The particular curvature or shape of the wall may vary somewhat although for most screening procedures an arcuate or convex shape consistent with the curvature of the upper portion of the breast is preferred. Also, as best seen in FIG. 3, wall 48 slopes upwardly and forwardly from bottom wall 44 to generally conform to the conical configuration of the upper half of the breast. In the event needle localization procedures are necessary, apertures 66 may be provided in selected suitable locations in the bottom wall.

Lower support plate 24 is also best seen in FIGS. 2 and 3 and is provided with planar top surface 25, anterior wall 54, opposite side walls 56, 57 and posterior wall 58. The upper surface 25 of plate 25 serves as the lower compression surface. The anterior wall 54 of the compression plate is curved, preferably arcuate, defining a relieved area 65 in the plate. As best seen in FIG. 3, anterior wall 54 inclines downwardly and forwardly from planar wall 25. The lower compression plate rests on support plate 21 and is secured by retaining clips 27 arranged on the opposite side walls which engage the opposite sides of the fixed support plate. Other types of fasteners such as suction cups may also be utilized to removably secure the lower compression plate to the support table 21 of the X-ray machine.

Compression plate 22 may be made from any suitable material which would not interfere with the passage of X-rays and which is suitably rigid to maintain parallelism with the compression plate. Again, lucite, plexiglas, or other polymeric materials are suitable for this purpose.

A better understanding of the invention will be had from the following description of use. During mammographic examinations using the improved compression plate design of the present invention, a breast of the patient is placed on the lower compression plate 24 and the compression plate 24 is lowered so that the breast is compressed between the upper compression plate 30 and the lower compression plate. Application of uniform pressure to the breast during the procedure results in improved diagnostic quality of the resulting radiographic images. A suitable film cassette is inserted into the film holder or recess 24 and the X-ray apparatus energized. Generally while the X-ray is exposed, the patient remains in a stationary position with respect to the mammography apparatus. Apertures 66 allow needle localization procedures, if necessary. The X-ray source 14 and support column 20 for the compression support plates are generally rotatable with respect to the cabinet 12 so that various mammographic projections can be made, as for example craniocaudad, 90° medio lateral and 45° mediolateral.

Figure 8:
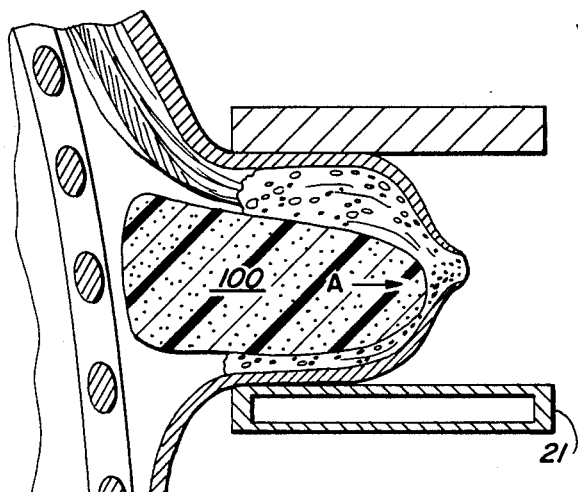
FIG. 8 is a cross-sectional view of a portion of a patient's breast compressed between a support table and a compression plate illustrating mammography technique using prior art support table and compression plates.
Figure 9:
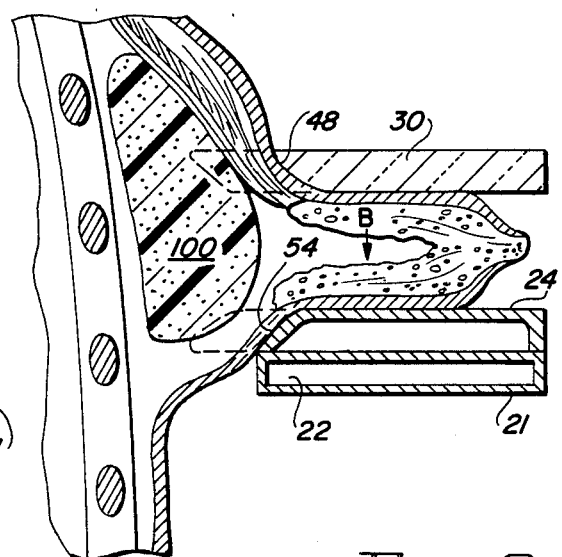
FIG. 9 is a cross-section of a portion of a patient's breast with the breast in a compressed position between the upper and lower compression plates of the present invention.

FIGS. 8 and 9 illustrate the advantages of the mammography apparatus of the present invention as applied to patients with prosthetically augmented breasts. FIG. 8 illustrates mammography procedure on a patient having a breast implant using conventional prior art support and compression plates. In this cross-sectional view, the breast is shown in a compressed condition as would occur in a standard craniocaudad mammographic projection. With conventional compression and support table apparatus, the prosthesis 100 becomes trapped in the position shown between the upper and lower portions of the breast tissue which causes pressure to be applied to the breast tissue in the direction arrow A. This force is 90° displaced from the desired force direction, which is indicated by arrow B in FIG. 9. Accordingly, it will be seen that with X-ray radiation impinging downwardly, the prosthesis may obscure all but a peripheral edge of the breast tissue to the field of view of the X-ray apparatus. The disadvantage is that for a complete and thorough examination, further projections with significantly increased radiation exposure to the patient may be required.

FIG. 9 is a view similar to FIG. 8 which illustrates the mammography procedure utilizing the compression plates 22 and 30 of the present invention. The configuration of the anterior walls 48 and 54, respectively, of the upper compression plate 30 and lower compression plate 24 prevent the prosthesis 100 from being trapped in the breast tissue between the plates. Walls 48 and 54 are both transversely curved and vertically sloped, allowing the prosthesis 100 to assume a position against the chest of the patient, as seen in FIG. 9. The breast tissue, due to its attachment to the skin layer and its ability to slide free of the underlying prosthesis will be selectively compressed apart from the prosthesis. The sloped surfaces of anterior walls, particularly wall 48 of the upper compression plate, provide additional skin contact to assist in drawing the breast tissue downwardly and forwardly away from the prosthesis. Obscuration of the tissue by the prosthesis and undesirable forward compression of the tissue exerted by the prosthesis are avoided.

Figure 4:
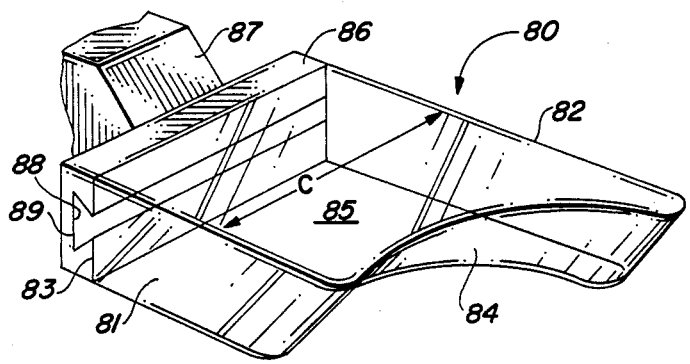
FIG. 4 is a perspective view of an alternate embodiment of a lower compression plate for mammograph examinations.

FIG. 4 shows an alternate embodiment of the present invention in which the upper compression plate 80 is of reduced transverse dimension "C" as compared to the compression plate shown in FIG. 2. The reduced dimensional size allows the compression plate to be used if the attending medical personnel wish to apply localized compression to a portion of the breast. Compression plate 80 has a body with opposite side walls 81, 82, planar bottom wall 85, posterior wall 83 and anterior wall 84. Compression is applied by the lower side of planar compression wall 85. Anterior wall 84 is shown having a curved configuration in which only a portion of the arcuate configuration of the corresponding wall of the plate is shown in FIG. 2. Surface 84 is downwardly sloped as shown conforming to the shape of the breast.

Plate 80 is transversely movable on slide member 86 which is mounted on connector 87 attachable to the X-ray machine. Slide 86 has a groove 88 which cooperates with tongue 89 on rear wall 83. Since plate 80 is transversely movable, the plate may be selectively adjusted to compress the desired section of the breast, for example, the area in one upper quadrant. Similarly, the compression plate may be conveniently detached from the slide and replaced with another plate of a different size or configuration. In other respects, the construction of the compression plate is has been described above.

Figure 5:
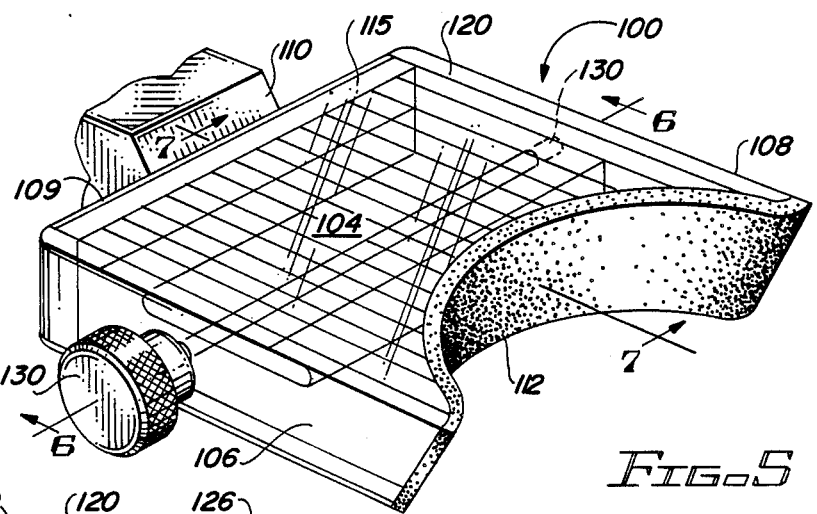
FIG. 5 is a perspective view of still another embodiment of a compression plate constructed according to the present invention.
Figure 6:
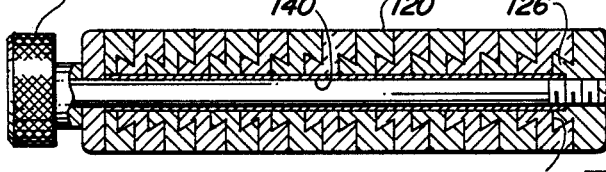
FIGS. 6 and 7 are sectional views taken, respectively, along section lines 6—6 and 7—7 of FIG. 5.
Figure 7:
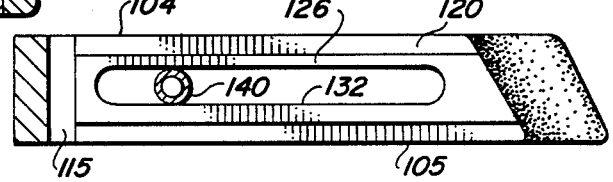

FIGS. 5, 6 and 7 show still another embodiment of the present invention which is generally designated by the numeral 100. In these drawing figures, a modified compression plate is shown in which the anterior breast-engaging surface may be selectively shaped to conform to various anatomical breast conditions. The modification is illustrated in connection with the upper compression plate but would also be applicable to the construction of the lower compression plate.

The modified compression plate 100 has an upper surface 104 and a lower compression surface 105. Opposite side walls 106, 108 and rear wall 109 form a unitary, generally U-shaped frame. Rear wall 109 has an integrally formed connector 110 attachable to the X-ray machine. Since the plate shown is the upper compression plate, front or anterior wall 112 slopes downwardly and outwardly from surface 104 and is rearwardly convex to conform to the patient's breast area.

Wall 112 extends between the side walls 106, 108 and is fabricated from a pliable material such as silastic and can be selectively contoured into the preferred shape in accordance with the anatomical requirements of the patient at the time of the examination. To accomplish this, a plurality of strips 120 of plastic or similar material are arranged in parallel fashion within the frame with an appropriate clearance space 115 provided at the rear of the strips. The individual strips are engaged to be relatively slideable to one another due to the groove 125 which receives an appropriate tongue 126 of the next adjacent strip. Anterior or posterior movement of the strips will impart movement to the pliable end wall 112 in the area of its point of attachment to the strip. Thus, by selective adjustment of the strips relative to one another, the configuration of surface 112 can be varied to accommodate the requirements of the patient. This is best illustrated in FIG. 7.

Once the strips nave been adjusted and the desired configuration of surface 112 established, strips 120 are locked into the desired position by tightening bolt 130 which has a threaded body 135 engageable within internally threaded tube 140 extending transversely through longitudinal slots 132 in the plates. By tightening locking bolt 130, transverse pressure is applied to the plates locking them into the selected position.

Figure 10:
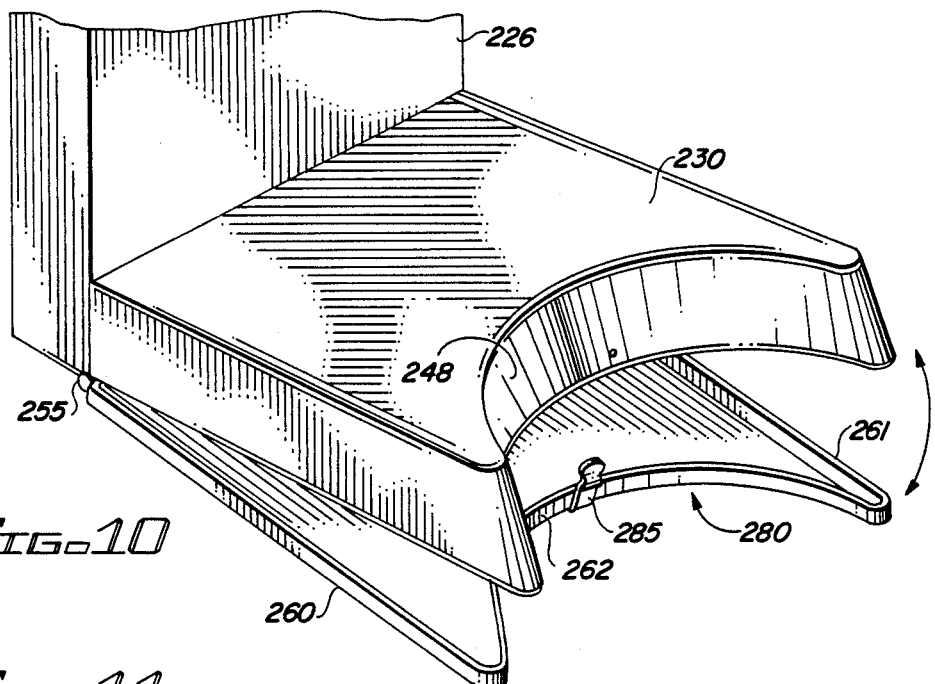
FIG. 10 is a perspective view of the lower compression plate as modified to receive a specially configured film cassette and also to assume the functions of compression and support.

FIG. 10 illustrates still another embodiment of the present invention which is generally designated by the numeral 200. In this embodiment, the lower compression plate 230 is shown supported in a generally horizontal position on the X-ray machine 226 in a position aligned with the X-ray tube to receive X-ray radiation. As has been described with reference to other embodiments, the lower compression plate has a relieved anterior surface 248 which is both curved and sloped to conform to the configuration of the patient's breast area. A cassette holder 280 is secured to the X-ray 226 apparatus at pivotal hinge member 255. Cassette holder 250 has opposite parallel edges 260 and 261 and forward or anterior edge 262. Edges 260 and 261 generally correspond to the edges of the compression plate 230 and the anterior edge 260 of the cassette holder conforms in shape to the lower edge of anterior wall 248 of the compression plate. Thus, a film holder or magazine in a shape generally corresponding to the shape of the adjacent compression plate 230 is provided. A specially configured film cassette, not shown, is insertable in the film magazine 280 with the film holder in the open position. Thereafter, the film magazine is pivoted to a closed position and secured in place at lock member 285. The advantage of the configuration shown in FIG. 10 is that a more complete X-ray photograph is provided the examining physician.

Figure 11:
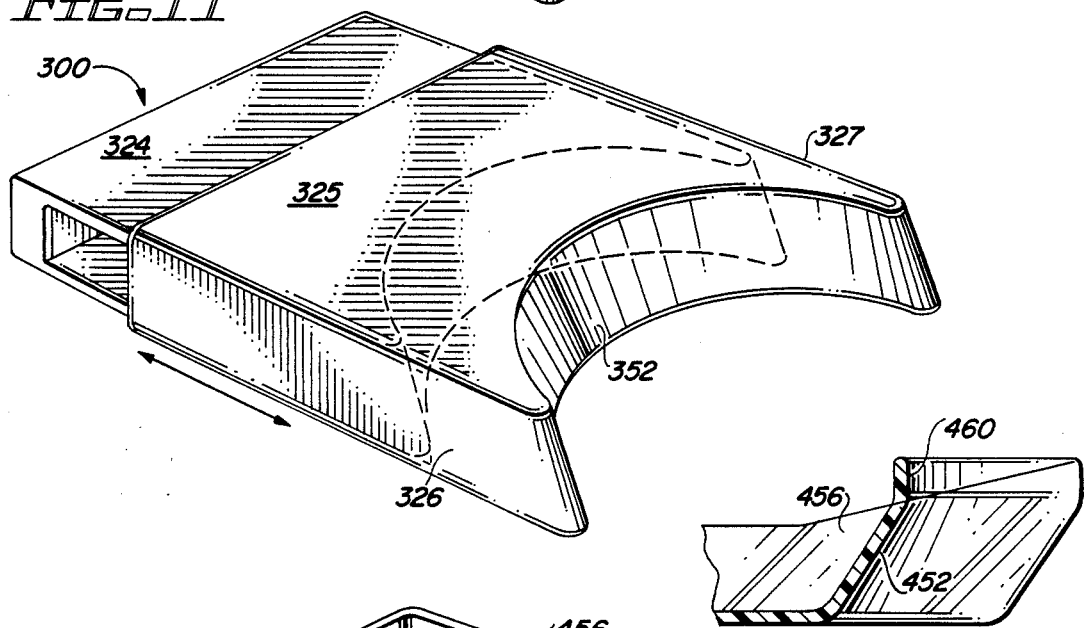
FIG. 11 is a perspective view of an alternate embodiment of the present invention in which the compression plate is configured as an extension having a relieved section secured over the conventional lower support plate.

In FIG. 11 still another embodiment is shown which is generally designated by the numeral 300. The lower fixed table 324 is part of the X-ray machine is conventional. The improved lower compression plate 325 has opposite side walls 326, 327 which are parallel and spaced apart a distance closely approximating the distance between the side walls of the lower fixed table 324. The forward or anterior edge 352 of the compression plate 352 is relieved and sloped as has been described to conform to the shape of the breast of the patient to accommodate the prosthetically augmented breast. As shown in FIG. 11, the compression plate 325 can be conveniently engaged on the fixed plate 324 with the side walls 326, 327 of the compression plate engaging the side walls of the table. The use of a flexible material permits the compression plate side walls to be easily expanded to facilitate placement of the plate on the lower support. When in place, compression plate 325 can be moved anteriorly or posteriorly along the support plate 324 as required. When the X-ray procedures are completed, the compression plate 325 can be quickly disengaged from the support table and the film cassette removed. The "snap-on" configuration of the compression table attachment permits a compression plate of the desired shape to be conveniently attached to the machine.

Figures 12, 13:
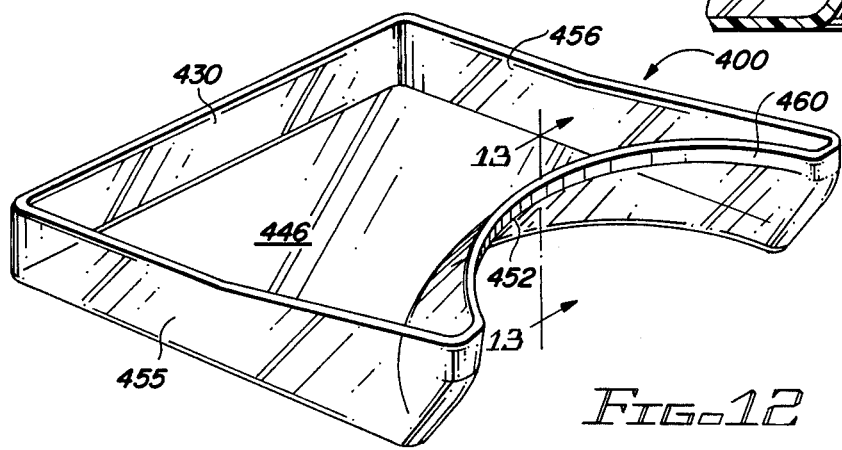
FIG. 12 is a perspective view of a modified form of the compression plate having a breast-retaining and confining wall.

In FIG. 12, another embodiment of the present invention is generally shown designated by the numeral 400. In this embodiment, an upper compression plate 430 is shown which is constructed generally as has been described with reference to FIGS. 1 to 3. In this embodiment, compression is again applied by compression surface 446 being brought into contact with the breast of the patient with the breast being supported on a lower compression plate having a relieved area as described above. However, to better contain the breast of the patient, the upper edge of the anterior wall 452 is extended upwardly beyond the upper edge of side walls 455, 456 a predetermined distance as, for example, 2 cm. Further, the opposite edges of this wall are extended posteriorly connecting with the opposite side edges 455 and 456 of the compression plate. Thus, in the case of an upper compression plate, the wall extension will extend toward the patient following the general contour of the upper portion of the breast. The upper edge of the extension wall 452 has a vertically-extending lip 460, typically having a height of about 2 cm. which further assists in containing the breast during the mammography procedure.

Thus it ill be seen that the present invention provides an improved mammography apparatus and a preferred form of the invention has been illustrated in the application. It is to be understood that various modifications, alterations and changes may be made thereto without departing from the spirit and scope of the appended claims. They are intended to be encompassed therein.

I claim:

1. In a mammographic device for examination of a patient having an augmentation prosthesis, said device having an X-ray source for emitting X-ray radiation along a predetermined path to expose an X-ray film and including a breast-support table positioned in said path, the improvement comprising a first compression plate disposed in said X-ray path above said support table and selectively movable relative to said support table to compress the breast during examination, said compression plate having a first generally planar compression surface adapted to engage the breast with an anterior edge of the plate positioned adjacent the patient, said anterior edge defining a relieved area generally shaped and adapted to compress substantially only breast tissue and to exclude the said prosthesis during compression and examination.

2. The device of claim 1 wherein said first compression plate is plastic.

3. The device of claim 1 wherein said first compression plate is at least partially transparent.

4. The device of claim 1 wherein said first compression plate defines one or more apertures to provide access to the patient's breast for needle localization procedures.

5. The device of claim 1 wherein said relieved area is generally arcuate in shape.

6. The device of claim 1 wherein said anterior edge forms the edge of an anterior wall inclined upwardly and generally toward the patient.

7. The device of claim 6 wherein said anterior wall extends a sufficient distance to engage and retain the upper breast area.

8. In a mammographic device for examination of a patient having an augmentation prosthesis, said device having an X-ray source for emitting X-ray radiation along a predetermined path to expose an X-ray film and including a breast-support table positioned in said path, the improvement comprising:

(a) a first compression plate disposed in said X-ray path and selectively movable relative to said breast-support plate to compress the breast during examination, said first compression plate having a first generally planar compression surface adapted to engage the breast with an anterior edge of the plate positioned adjacent the patient, said anterior edge defining a relieved area generally shaped and adapted to exclude the said prosthesis during compression and examination; and (b) a second compression plate associated with said breast support table, said second compression plate having a second generally planar compression surface oppositely disposed relative to said first compression surface and adapted to support the breast during examination, said second compression plate having an anterior edge positioned adjacent the patient, said anterior edge defining a relieved area generally shaped and adapted to exclude the said prosthesis during compression and examination whereby primarily only breast tissue is compressed.

9. The device of claim 8 further including film holder means associated with said second compression plate defining a film-receiving magazine.

10. The device of claim 8 wherein said first and second compression plates each have attachment means for removably attaching said plates to the X-ray machine.

11. The device of claim 8 wherein said second compression plate has a wall inclined downwardly and generally toward the said patient from said support surface edge.

12. The device of claim 11 wherein said wall extends a sufficient distance to engage and retain the upper breast area.

* * * * *